US008816856B2

(12) United States Patent
Whitehouse et al.

(10) Patent No.: US 8,816,856 B2
(45) Date of Patent: Aug. 26, 2014

(54) MEDICAL INSTRUMENT CLEANING SYSTEM AND METHOD

(75) Inventors: Alan B. Whitehouse, Augusta, GA (US); Keith A. Lynn, Johnson, SC (US); Stephen W. Smith, Martinez, GA (US)

(73) Assignee: Augusta E.N.T., P.C., Augusta, GA (US)

( * ) Notice: Subject to any disclaimer, the term of this patent is extended or adjusted under 35 U.S.C. 154(b) by 574 days.

(21) Appl. No.: 12/883,212

(22) Filed: Sep. 16, 2010

(65) Prior Publication Data

US 2011/0084835 A1 Apr. 14, 2011

Related U.S. Application Data

(60) Provisional application No. 61/250,887, filed on Oct. 13, 2009.

(51) Int. Cl.
*G08B 13/14* (2006.01)
*G06Q 10/00* (2012.01)

(52) U.S. Cl.
USPC ............ 340/572.1; 340/568.1; 705/2; 705/28

(58) Field of Classification Search
USPC .............. 340/505, 506, 521, 552, 568.1, 571, 340/572.1, 572.4, 572.7, 572.8, 10.1; 235/462.1, 470, 487, 492, 494, 381, 235/385; 705/2, 7.18, 28; 700/24, 89, 90; 134/57 R, 123, 172, 173; 600/112, 132; 436/15; 422/24, 408
See application file for complete search history.

(56) References Cited

U.S. PATENT DOCUMENTS

| 3,963,438 | A | | 6/1976 | Banez |
| 5,090,433 | A | | 2/1992 | Kamaga |
| 5,225,160 | A | | 7/1993 | Sanford et al. |
| 5,339,800 | A | | 8/1994 | Wiita et al. |
| 5,609,561 | A | * | 3/1997 | Uehara et al. ................. 600/112 |
| 5,761,069 | A | | 6/1998 | Weber et al. |
| 6,106,691 | A | | 8/2000 | Nakamura et al. |
| 6,439,577 | B2 | * | 8/2002 | Jorgensen et al. ............ 277/374 |
| 6,641,781 | B2 | | 11/2003 | Walta |
| 6,858,181 | B2 | * | 2/2005 | Aoyagi ........................... 422/24 |

(Continued)

FOREIGN PATENT DOCUMENTS

| JP | 2002175376 A | 6/2002 |
| JP | 2007325724 A | 12/2007 |

OTHER PUBLICATIONS

Written Opinion and International Search Report dated Apr. 27, 2011 of corresponding International PCT Application No. PCT/US2010/049582, filed Sep. 21, 2010.

*Primary Examiner* — Van T. Trieu
(74) *Attorney, Agent, or Firm* — Pearne & Gordon LLP

(57) ABSTRACT

A system and method for monitoring a status of a medical instrument is provided. Using an input peripheral associated with a computer terminal, a code associated with the medical instrument to be subjected to a cleaning operation after a previous use of the medical instrument is received. A timer for monitoring a duration of the cleaning operation is initiated. In response to completion of the cleaning operation determined based on the timer, a status of the medical instrument in an electronic record associated with the medial instrument stored in a non-transitory computer-readable medium is updated to indicate that the medical instrument has been cleaned. An indication that the cleaning operation being performed on the medical instrument is complete is then issued.

19 Claims, 3 Drawing Sheets

(56) References Cited

U.S. PATENT DOCUMENTS

| | | |
|---|---|---|
| 7,061,597 B2 | 6/2006 | Oberleitner et al. |
| 7,547,552 B2 * | 6/2009 | Doi et al. .................. 436/15 |
| 7,818,182 B2 * | 10/2010 | Giraldo et al. .................. 705/2 |
| 8,276,603 B2 * | 10/2012 | Berklund et al. ............. 134/123 |
| 2002/0159917 A1 | 10/2002 | Swart et al. |
| 2002/0161460 A1 * | 10/2002 | Noguchi ........................ 700/90 |
| 2007/0041864 A1 | 2/2007 | Forsyth et al. |
| 2007/0267039 A1 * | 11/2007 | Sullivan ........................ 134/1 |
| 2007/0286764 A1 | 12/2007 | Noguchi et al. |
| 2008/0162184 A1 | 7/2008 | Matsubara et al. |
| 2008/0219899 A1 | 9/2008 | Deshays |
| 2008/0236631 A1 | 10/2008 | Lin et al. |
| 2008/0300553 A1 | 12/2008 | Irion et al. |
| 2009/0008238 A1 | 1/2009 | Williams |
| 2009/0055215 A1 | 2/2009 | Giraldo et al. |
| 2009/0196794 A1 | 8/2009 | Smith et al. |
| 2009/0217956 A1 | 9/2009 | Noguchi et al. |
| 2009/0272806 A1 * | 11/2009 | Kemp et al. ................. 235/462.1 |
| 2010/0030573 A1 * | 2/2010 | Araki et al. ........................ 705/2 |

\* cited by examiner

MEDICAL INSTRUMENT CLEANING SYSTEM AND METHOD

CROSS-REFERENCE TO RELATED APPLICATIONS

This application claims the benefit of U.S. Provisional Application No. 61/250,887, filed Oct. 13, 2009, the entirety of which is incorporated herein by reference.

BACKGROUND OF THE INVENTION

1. Field of the Invention

This application relates generally to a method and apparatus for cleaning medical instruments, and more specifically to a computer-based method and system for documenting cleansing procedures performed on a medical instrument to distinguish between a medical instrument that is ready for use and a medical instrument that is not ready for use.

2. Description of Related Art

Various types of medical treatment call for the use of medical instruments such as endoscopes, for example, that are at least partially inserted into a patient's body. These endoscopes and other such instruments can be extended through an orifice or small surgical incision into the patient's body to provide a treating physician with a view of, or access to internal organs or other portions of interest. Such instruments eliminate the need to physically expose the internal portion of the patient that is of interest to the physician to allow for inspection of that internal portion and less invasive treatment of the patient.

Endoscopes and other medical instruments that can be at least partially inserted into patients must be thoroughly cleansed before being used to treat different patients. Ear-nose-and-throat specialists, for example, commonly use scopes that include an elongated, flexible fiber-optic lens that is to be inserted through a patient's nostril and into the patient's sinus cavity or throat. Scopes can also have a substantially-rigid lens to be used when the lens does not need to navigate an arcuate path to reach the portion of the patient that is of interest.

Both types of lenses can be removed from the scope to be cleaned, and typically include a bundle of optical fibers wrapped by a protective sheath made of a rubber, plastic or other suitable material. The substantially-rigid lenses are more durable than the flexible lenses, and can withstand the conditions within an autoclave during cleaning operations. The flexible lenses, in contrast, can not be autoclaved and must be submerged within an enzymatic or other suitable cleaning solution to be thoroughly cleaned. Additionally, the flexible scope lenses must be subjected to pressure tests to detect the presence of any cuts or other defects in the protective sheath wrapped about the bundle of optical fibers.

The status of a scope lens or other medical instrument as having been cleaned or needing to be cleaned can not be readily detected by the human eye. Further, any cuts or other such damage to the sheath provided to the flexible lenses, for example, are also not readily observable. Conventional record-keeping systems typically include manually marking the status of scope lenses or other medical instruments as being ready for use, or requiring cleaning and/or servicing. However, such record-keeping systems are limited in their effectiveness by factors such as illegible handwriting on labels and other human errors such as confusing one scope lens with another.

SUMMARY

Accordingly, there is a need in the art for a method and system of maintaining and monitoring a status of a lens or other medical instrument capable of transmitting an ailment from one patient to another. Such a method and system can minimize manual input of information by an operator, and can include the use of a computer-readable code provided to each such medical instrument that can be read to reliably determine the status of that medical instrument.

According to one aspect, the present technology involves a method for monitoring a status of a medical instrument. According to the method, and using an input peripheral associated with a computer terminal, a code associated with the medical instrument to be subjected to a cleaning operation after a previous use of the medical instrument is received. A timer for monitoring a duration of the cleaning operation is initiated. In response to completion of the cleaning operation determined based on the timer, a status of the medical instrument in an electronic record associated with the medial instrument stored in a non-transitory computer-readable medium is updated to indicate that the medical instrument has been cleaned. An indication that the cleaning operation being performed on the medical instrument is complete is then issued.

According to another aspect, the present technology also involves a method of monitoring a status of an endoscopic medical instrument including a housing that is to be at least partially inserted into a patient. The method includes receiving, using a barcode scanner, a code associated with the endoscopic medical instrument to be subjected to a cleaning operation after a previous use of the endoscopic medical instrument with another patient. A query of an electronic record associated with the endoscopic medical instrument and stored in a non-transitory computer-readable medium is initiated to determine whether the endoscopic medical instrument was cleaned after a most-recent use of the endoscopic medical instrument with the another patient. A selection of a first cleaning station, from among a plurality of available cleaning stations, to be used for performing the cleaning operation of the endoscopic medical instrument is received. In response to receiving the selection of the first cleaning station, a timer is initiated for timing a duration of the cleaning operation. In response to completion of the cleaning operation determined based on the timer, a status of the endoscopic medical instrument in the electronic record is updated to indicate that the endoscopic medical instrument has been cleaned since the most-recent use with the another patient. An indication that the cleaning operation being performed on the endoscopic medical instrument is complete is then issued.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1:
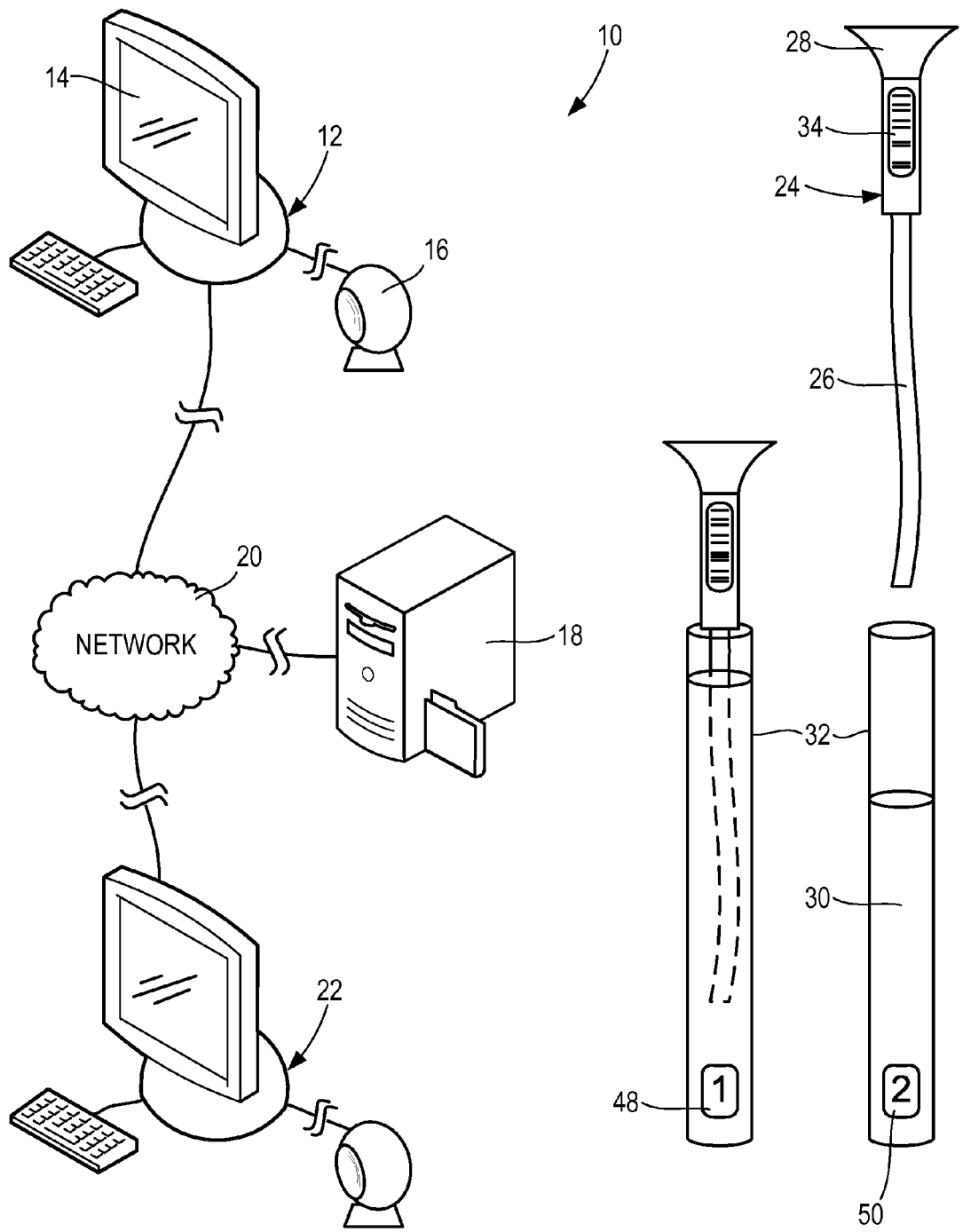
FIG. 1 shows an illustrative embodiment of a cleaning station arrangement for performing a cleaning operation on a medical instrument and a computer system for monitoring a status of the medical instrument.

Certain terminology is used herein for convenience only and is not to be taken as a limitation on the present invention.

Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows an illustrative embodiment of a computer system 10 for implementing a method of monitoring the status of a medical measurement. As shown, the computer system 10 includes a computer terminal 12 that comprises a touch-sensitive display panel 14 and an input peripheral in the form of a barcode scanner 16. A microprocessor provided to the computer terminal 12 can execute computer-executable instructions stored on a non-transitory computer-readable medium to carry out the various method steps described herein.

The computer terminal 12 can optionally be connected to a database server 18 or other suitable non-transient computer accessible storage terminal over a communication network 20 such as the Internet and/or a local area network ("LAN"), for example, to store information received by the computer terminal 12, used to monitor the status of medical instruments, or a combination thereof as described herein. According to alternate embodiments, such information can optionally be stored locally by a non-transient computer-readable memory operatively connected, and provided locally to the computer terminal 12. Thus, the computer system 10 can include a computer terminal 12 that maintains the information locally, or can include multiple computer terminals including at least a second computer terminal 22 that is network connected with the computer terminal 12 as part of an enterprise solution. Such enterprise solutions can optionally store the information regarding the status of medical instruments on the database server 18 to ensure that the information is available over the communication network 20 at various locations where the medical instrument may be employed to treat a patient.

Although the present invention can be utilized to monitor the status of any medical instrument, for the sake of brevity the system and method will be described herein is monitoring the status of a fiber optic lens 24 that can be operatively connected to an optical scope. The lens 24 can be at least partially inserted into a patient and includes a bundle of optical fibers that extend through a protective sheath 26 to transmit light from inside the patient to the optical scope (not shown) used by a physician to view the internal portions of the patient with minimal tissue damage.

The optical fibers provided to the lens 24 are at least partially encapsulated within the protective sheath 26 that can be made from a plastic, rubber, or other suitably flexible material. Between uses, the lens 24, or at least a portion of the sheath 26 that was inserted into a patient, must be cleaned to minimize the presence of contaminants on the lens 24. A mounting portion 28 of the lens 24 does not come into contact with patients and is thus not required to be submerged within a cleaning solution as described in detail below. The mounting portion 28 serves to operatively connect the lens 24 to the optical scope used by the physician to view the internal portions of the patient.

To clean the lens 24, the lens 24 is to be detached from the optical scope and at least a portion of the sheath 26 submerged within a cleaning solution 30 stored by a cleaning station 32. The cleaning solution 30 can include any suitable disinfectant, cleaner, sterilant, enzymatic detergent, or a combination thereof. For example, the cleaning solution 30 according to one embodiment can include one or more members of the family of cleaning materials offered for sale under the trade name Cidex®. After being used with a patient, the portion of the sheath 26, for example, is to be submerged within the cleaning solution 30 in the cleaning station 32 for a predetermined period of time, such as 12 minutes. The predetermined period of time for which the optical portion 26 must be submerged within the cleaning solution 30 is dependent upon the specific cleaning solution 30 used, and is sufficient to minimize the presence of contaminants on the lens 24.

Since the optical fibers of the lens 24 are at least partially encapsulated within an internal passage defined by the protective sheath 26, the lens 24 is also to be pressure tested to detect any breaches in the protective sheath 26 such as cuts that may result over time from ordinary use of the lens 24. Such breaches in the protective sheath 26, if not repaired, can permit the cleansing solution 30 and possibly other contaminants to enter the internal passage defined by the sheath 26 through which the optical fibers extend. Such contaminants are to be eliminated before the lens 24 is subsequently used on another patient. Lenses 24 that are determined to include a breach of the sheath 26 during pressure testing or other structural damage should be designated as being "locked out", requiring servicing of the sheath 26 to repair any such structural damage or optionally replacement of the sheath 26 before that lens 24 can once again be used to treat patients.

To identify each lens 24 and distinguish it from other lenses 24, a barcode 34 are other computer-readable code is associated with the lens 24. As shown in FIG. 1, the barcode 34 is adhesively affixed adjacent to the connector portion 28 where it will not be submerged within the cleaning solution 30 while the lens 24 is being cleaned. The barcode 34 or other computer readable code provided to each lens 24 is unique, and therefore serves to distinguish the lenses 24 from each other. As described in detail below, the barcode 34 or other computer readable code is utilized according to a method to minimize the likelihood that a patient will be examined using a lens 24 having a status other than "ready for use." Although any suitable computer-readable code such as an RFID tag, inductive transmitter, digital transmitter, etc. . . . can be used, the method and system are described in detail below as including a barcode 34 as the computer-readable code.

Figure 2:
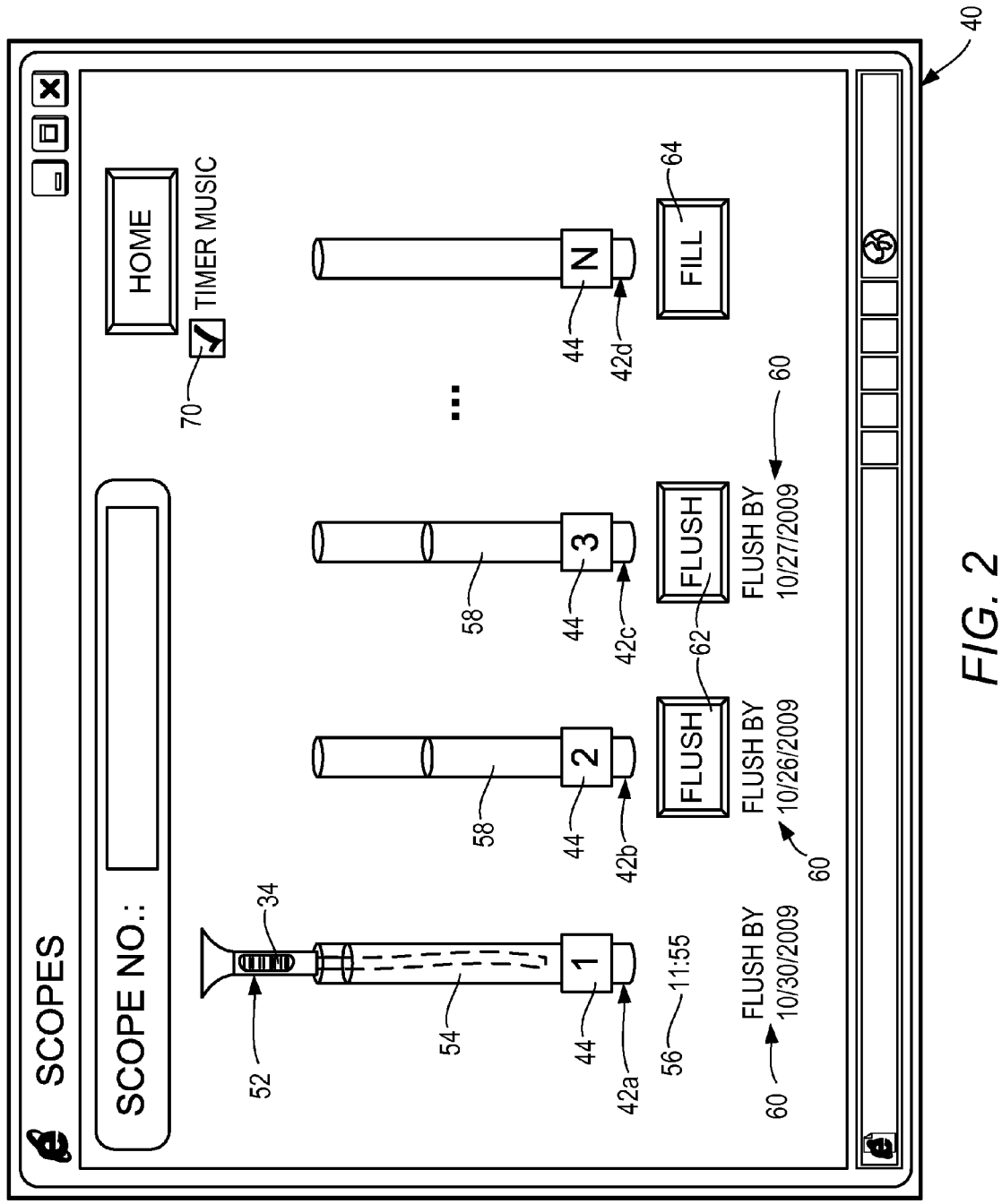
FIG. 2 shows an illustrative embodiment of a computer-generated monitoring interface utilized in monitoring a status of a medical instrument.
Figure 3:
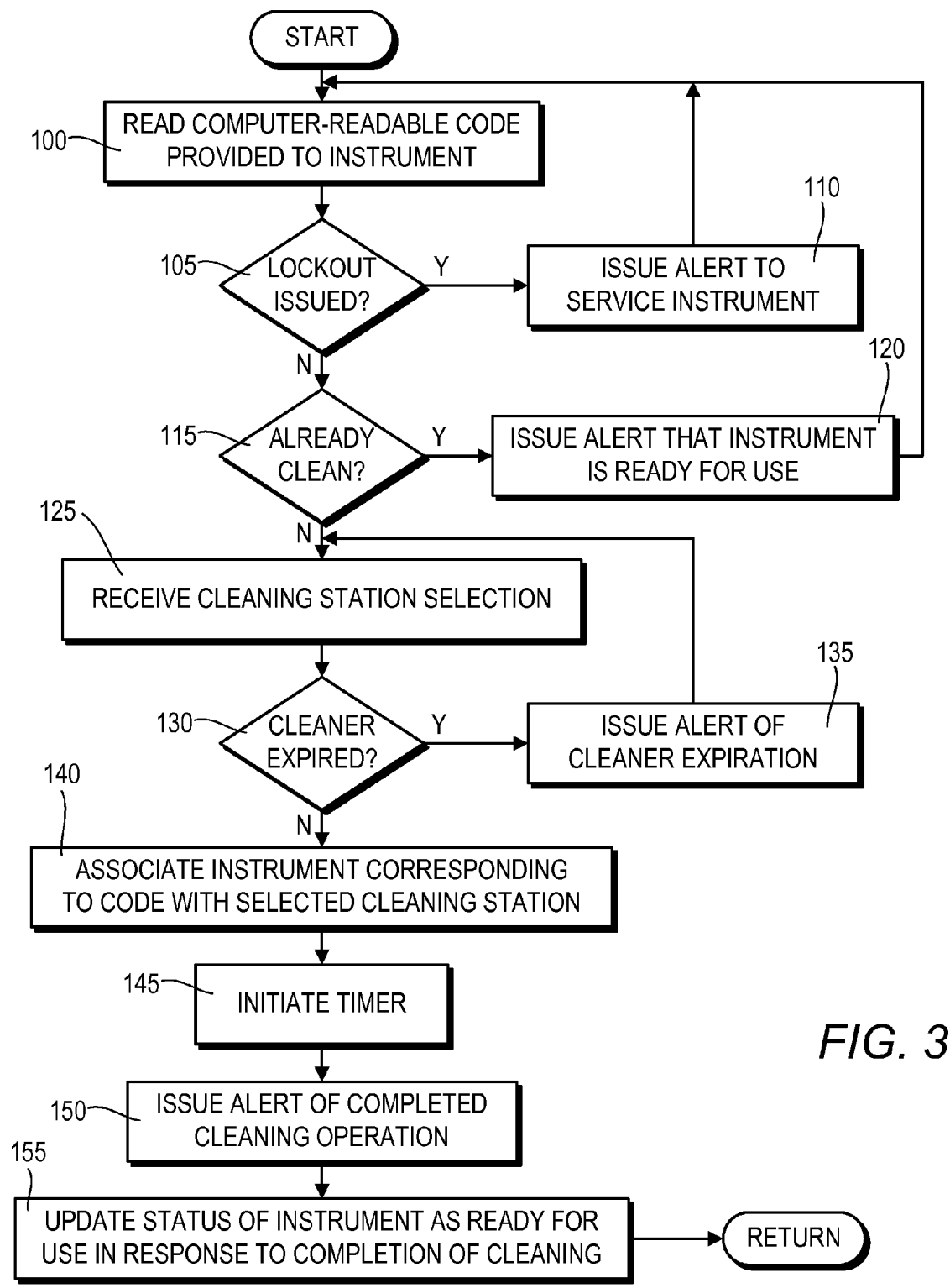
FIG. 3 is a flow diagram illustrating an embodiment of a method of using a computer system to monitor the status of the lens.

Use of the computer system 10 to implement an embodiment of a method of monitoring the status of medical instrument such as the lens 24 can be understood with reference to FIGS. 2 and 3. FIG. 2 shows an embodiment of a cleansing monitoring interface 40 generated by the computer system 10 in response to execution of computer-executable instructions stored on a computer-readable medium that is accessible to the computer terminal 12 (FIG. 1), database server 18, or a combination thereof. The interface 40 can be generated by the execution of code based on HTML, for example, and displayed by the touch-sensitive display panel 14 in a web browser or other suitable computer application operating on the computer terminal 12. As shown, the interface 40 includes a plurality of cleaning stations 42a-d displayed as computer-generated graphics by the touch-sensitive display panel 14. Each cleaning Station 42a-d in the interface 40 is labeled with a numerical label 44 or other suitable label that represents a similar label provided to corresponding cleaning stations 32 in which the portion of the lens 24 can be placed to be cleansed. Thus, the cleaning stations 42*a-d* are displayed within the interface 40 in a manner so that they correspond to the actual cleaning stations 32 used to clean the lenses 24, and this correspondence can be readily ascertained by technician presented with the interface 40 by the touch-sensitive display panel 14. For the embodiments shown in FIGS. 1 and 2, one of the cleaning stations 32 labeled with the label 48 that reads "1" in FIG. 1 corresponds to the virtual cleaning station 42*a* shown in the interface 40 also provided with numerical label 44 displaying the number "1". Likewise, the actual cleaning station 32 labeled with a label 50 that reads "2" in FIG. 1 corresponds to the virtual cleaning Station 42*b* appearing in the interface 40 and associated with the numerical label 44 that reads "2" as shown in FIG. 2, and so on.

Referring once again to FIG. 2, cleaning Station 42*a* is graphically displayed in the interface 40 as having a portion of a lens 52 submerged within a cleaning solution 54. Again, the virtual lens 52 submerged within cleaning solution 54 at cleaning station 42*a* is a graphical depiction representing an actual lens 24 that is at least partially submerged within the actual cleaning station 32 provided with the label 48 that reads "1" as shown in FIG. 1. This graphical representation displayed by the touch-sensitive display panel 14 serves as an indication to a technician that the lens 24 is currently disposed within the cleaning solution 30 of the cleaning station 32 with the label reading "1" and is undergoing a cleaning operation. The virtual lens 52 is said to be "virtual" because it is a computer-generated graphic representing the corresponding lens 24 disposed within the cleaning solution 30 of the cleaning station 32 with the label reading "1" in FIG. 1.

In response to the start of a cleaning operation at the cleaning station 32 with the label 48 reading "1" in FIG. 1, a time 56 indicating the time remaining until completion of the cleaning operation can be displayed adjacent to the cleaning Station 42*a* in the interface 40 shown in FIG. 2. Cleaning operations require the lens 24 to remain submerged within the cleaning solution 30 for a predetermined period of time, which is 12 minutes according to the illustrative embodiment. According to other embodiments, this predetermined period of time can be longer or shorter, and can optionally be specific to the requirements and effectiveness of the cleaning solution 30 employed for a particular cleaning operation. In response to the starting of the cleaning operation, the time 56 displayed in the interface 40 begins at 12 minutes and counts down until time expires, thereby indicating completion of the cleaning operation.

In contrast, cleaning stations 42*b* and 42*c* shown in the interface 40 are displayed without the graphical representation of the lens 52, indicating that the actual cleaning stations 32 corresponding to the virtual cleaning stations 42*b* and 42*c* are not currently in use, and are available to receive a lens 24 as part of a cleaning operation. Cleaning stations 42*b* and 42*c* are displayed as including a graphical cleaning solution 58 thereby indicating that their respective actual cleaning stations 32 also include an actual cleaning solution 30.

Cleaning Station 42*d* shown in the interface 40 appears empty, without a graphical representation of the cleaning solution 30 and without a graphical representation of the lens 52. Such a representation indicates that the actual cleaning station 32 represented in the interface 40 by the virtual cleaning station 42*d* is also empty, and is to be filled with cleaning solution 30 before the cleaning station 32 corresponding to the virtual cleaning station 42*d* is ready to perform a cleaning operation. Once cleaning solution 30 has been added to the actual cleaning station 32 represented by the virtual cleaning station 42*d*, the operator can select a "FILL" button 64 appearing as a soft key displayed by the touch-sensitive display panel 14 to indicate that the cleaning solution 30 has been added. In response to selection of the "FILL" button 64, the computer terminal 12 can record the date and/or time that the cleaning solution 30 was added, and automatically schedule a reminder to change the cleaning solution 30 following expiration of a predetermined period of time. This predetermined period of time can be specific to the cleaning solution 30, to an industry standard or mandate, or any other period of time during which the cleaning solution 30 can be considered effective to perform the cleaning operation. The reminder scheduled by the computer terminal 12 can be based, at least in part, on the internal clock and calendar of the computer terminal 12, the internal clock and calendar of the database server 18, a network signal, or other suitable date and/or time reference.

The interface 40 displayed by the touch-sensitive display panel 14 can also optionally display status information regarding the cleaning solution 30 in each of the cleaning stations 32. The cleaning solution 30 may have a maximum useful life during which it is effective, and recommended by the manufacturer of the cleaning solution 30 for cleaning lenses 24. Based on the date on which the cleaning solution 30 is added to each cleaning station 32 as indicated by selection of the "FILL" button 64 for each of the respective cleaning stations 42*a-d*, an expiration date 60 can be displayed adjacent to each of the virtual cleaning stations 42*a-d* displayed as part of the interface 40. The expiration date serves as a visible reminder to the technician not to use cleaning solution 30 beyond its expiration date 60 and to replace expired cleaning solution 30. Other indicators such as a color in which the cleaning stations 42*a-d* representing actual cleaning stations 32 with expired cleaning solution 30 can also optionally be used. Further, a selectable button such as the label 44 reading "1" for example, that can be selected by the operator to activate a countdown of the time 56 during a cleaning operation can optionally be made un-selectable following expiration of the cleaning solution 30. For example, the operator can optionally select the label 44 reading "1" in FIG. 2 using an input peripheral such as a mouse or simply by touching the label 44 on the touch-sensitive display panel 14 to commence a cleaning operation and start the countdown of the timer 56. For such an embodiment, an attempt to select this label 44 could fail to initiate the timer 56, and optionally audibly and/or visibly present the operator with a warning that the cleaning solution 30 represented by the virtual cleaning station 42*a* has expired.

When disposing of expired cleaning solution 30 the technician can enter the fact that the cleaning solution 30 has been, or is being replaced by selecting a "FLUSH" button 62 displayed as part of the interface 40. The technician can select the flush button 62 by physically touching the portion of the touch-sensitive display panel 14 (FIG. 1) where the FLUSH button 62 being selected is displayed. According to such an embodiment, each FLUSH button 62 is a soft key displayed by the computer terminal 12 executing computer executable instructions. The touch-sensitive display panel 14 transmits a signal in response to selection of the FLUSH button 62 to indicate to the computer system 10 that the expired cleaning solution 30 has been disposed of Again, selection of the FLUSH buttons 62, like any of the other buttons described herein, can be accomplished using an input peripheral such as a mouse, trackball, touchpad, keyboard, and the like.

According to alternate embodiments, the flush buttons 62 can optionally be concealed from view within the interface 40, and made visible as a reminder by the computer system 10 only after cleaning solution 30 within the cleaning station 32 has reached its expiration date 60, or is within a predetermined number of days, hours, etc. . . . of its expiration date 60. According to other embodiments, the flush buttons 62 are displayed and made available as part of the interface 40 anytime the cleaning solution 30 is stored by the cleaning station 32, allowing selection of the flush button 62 and disposal of the cleaning solution 30 as desired.

Information corresponding to the date and/or time at which expired cleaning solution 30 has been disposed of as indicated by selection of the flush buttons 62 can be stored on a computer-readable medium provided to the computer terminal 12, transmitted over the communication network 20 to be stored by the database server 18, or a combination thereof. Information concerning the date and/or time at which expired cleaning solution 30 is disposed of can be obtained from an internal clock provided to the computer terminal 12 or based on a clock signal accessible via the computer network 20, for example. Accordingly, a detailed record regarding handling of the cleaning solution 30 can be maintained.

An empty cleaning station 32 represented graphically within the interface 40 by virtual cleaning station 42d indicates a corresponding actual cleaning station 32 is available to be filled with new cleaning solution 30. When the new cleaning solution 30 is to be added to the cleaning station 32 corresponding to graphical cleaning station 42d the technician can select the "FILL" button 64 also displayed as a soft key by the touch-sensitive display panel 14 as part of the interface 40. Selection of the FILL button 64 establishes the date and time that the new cleaning solution 30 is being added to the cleaning station 32 corresponding to the virtual cleaning station 42d. Again, date and/or time information when the fill button 64 is selected by the technician can be obtained based on the internal clock of the computer terminal 12 or another date and/or time signal available over the communication network 20, and this information stored in an electronic record on a computer-readable medium provided to the computer terminal 12, to the database server 18 over the communication network 20, or a combination thereof.

Embodiments of the method include use of a predetermined cleaning solution 30 stored in an electronic record that is accessible by the computer system 10. Among the information known about the cleaning solution 30 being used is the useful life of the cleaning solution 30 from which the expiration date 60 can be determined. Upon selection of the fill button 64 via the interface 40 the computer system 10 can automatically, and without additional intervention from the technician aside from selection of the fill button 64, calculate the expiration date 60 based on the known useful life of the cleaning solution 30 to be filled within the cleaning station 32 and the time/date information determined from the internal clock of the computer terminal 12 or over the communication network 20. For example, for embodiments requiring a predetermined duration of a cleaning operation regardless of the cleaning solution 30 used, the expiration date 60 can be calculated as that predetermined period of time following selection of the FILL button 64.

According to alternate embodiments, when the cleaning solution 30 is added to a cleaning station 32, the technician can optionally scan a barcode or other computer-readable code associated with the cleaning solution 30 via barcode scanner 16 or other appropriate computer peripheral in communication with the computer system 10 to input the specific cleaning solution 30 being added. In response to reading this barcode or other computer-readable code provided to the bottle of cleaning solution 30, for example, information concerning the useful life of that cleaning solution 30 can be retrieved from an electronic database stored locally by the computer terminal 12 and/or remotely by the database server 18 over the communication network 20, or from another network accessible computer terminal 22 or other computer-readable medium. The information concerning the useful life of the cleaning solution 30 so obtained can then be used to calculate the expiration date of that cleaning solution being added relative to time and/or date information determined based on an internal clock of the computer terminal 12 or otherwise obtained over the communication network 20. But regardless of how it is determined, the expiration date 60 can be displayed as part of the interface 40 as shown in FIG. 2.

FIG. 3 is a flow diagram illustrating an embodiment of a method of using a computer system 10 to monitor the status of the lens 24. To be classified as "ready for use" the lens 24 is to have been cleaned subsequent to the most recent previous use of the lens 24 on a different patient. According to alternate embodiments, the lens 24 in question must also pass a pressure test subsequent to the previous use to determine whether the protective sheath 26 surrounding the bundle of optical fibers is free of breaches. If the pressure testing and/or cleaning operation has yet to be performed since it was last used, the lens 24 will be designated as "not ready for use". Should the lens 24 fail a pressure test, the lens 24 will be assigned a status of "locked out" to indicate that the lens 24 is not to be used to treat patients until breaches in the protective sheath 26 surrounding the bundle of optical fibers is repaired or the sheath 26 replaced. To assign the "locked out" status to a lens 24 a bar code 34 such as that shown in FIG. 1 can be scanned using the barcode scanner 16 and an appropriate menu item displayed within the interface 40 by the touch-sensitive display panel 14 selected.

Referring to the flow diagram of FIG. 3, before the lens 24 is used to treat a patient the barcode 34 is scanned using the barcode scanner 16 provided to the computer system 10 at step 100. In response to reading the barcode 34, the computer system 10 accesses an electronic record corresponding to the barcode 34 that was read to determine if a "locked out" status has been assigned to the lens 24 provided with that particular barcode 34 at step 105. If so, the computer system 10 transmits a signal that causes an alert to be displayed to the technician scanning the barcode 34 via the touch-sensitive display panel 14 at step 110. In addition to, or instead of the visible warning, the computer terminal 12 can optionally present the technician with an audible warning.

If it is determined at step 105 that a "locked out" status has not been issued for that particular lens 24, the computer system 10 also queries the electronic record at step 115 to determine whether that lens 24 has already been cleaned since it was last used. When the lens 24 is used the barcode 34 is scanned to indicate that the lens 24 is being used. If so, a signal is transmitted causing the touch-sensitive display panel 14 to display an alert at step 120 informing the technician that the lens 24 has already been cleaned and another cleaning operation is unnecessary.

If, however, a "locked out" status has not been issued and the lens 24 is in need of being cleaned, the technician can optionally be prompted to select the virtual cleaning station from the interface 40 corresponding to the actual cleaning station 32 to be used to perform or cleaning operation on the lens 24 having the barcode 34 that was scanned. In response to the technician's selection, the computer system 10 receives the selection at step 125 in FIG. 3. The technician can manually enter the selection of the virtual cleaning station corresponding to the desired actual cleaning station 32 by simply touching a portion of the touch-sensitive display panel 14 where the virtual cleaning station corresponding to the actual cleaning Station 32 to be used is displayed (e.g., such as by touching the label 44 that reads "1" in FIG. 2). According to alternate embodiments, the actual cleaning station 32 used by the technician can optionally be provided with a sensor to detect that a lens 24 is being inserted, and optionally identify the lens 24 to transmit the actual cleaning station 32 selected by the technician. As discussed above the technician should select a cleaning station 32 having cleaning solution 30 that has not yet reached its expiration date 60.

In response to receiving the technician's selection of the desired cleaning station 32 at step 125, the computer system 10 can compare date and/or time information obtained from the computer terminal's internal clock or over the communication network 20 to the expiration date 60 of the cleaning solution 30 in the selected cleaning station 32 to determine whether the cleaning solution 30 is expired at step 130. If so, the computer system 10 transmits a signal causing an alert to be displayed by the touch-sensitive display panel 14 at step 135 to inform the technician that the selected cleaning station 32 has expired cleaning solution 30. The technician can then elect to flush and replace the expired cleaning solution 30 or select a different cleaning station 32 by once again selecting a corresponding virtual cleaning station 42a-d from those displayed within the interface 40, thereby returning a method to step 125.

If the cleaning solution 30 in the selected cleaning Station 32 has not yet reached its expiration date 60 displayed within the interface 40, the computer system 10 associates the lens 24 provided with the scanned barcode 34 with the cleaning station 32 selected by the technician at step 140 for that cleaning operation. The association between the selected cleaning station 32 and the lens 24 with the scanned barcode 34 creates a record stored by a computer-readable medium accessible to the computer system 10 establishing that the lens 24 is being cleaned. Other information such as the status and type of the cleaning solution 30 in the selected cleaning station 32 can optionally also be recorded in the electronic record. A time 56 that is counted down as a timer to measure the progress of the cleaning operation is initiated at step 145 and displayed within the interface 40 as shown in association with the virtual cleaning station 42a to inform the technician of the time remaining before the cleaning operation is complete. The computer system 10 can optionally issue an alert informing the technician that the cleaning operation has been completed at step 150. The alert can simply be the display of the time 56 as "0:00" within the interface 40, but alternate environments include displaying a pop-up window or other visual display via the touch-sensitive display panel 14 to indicate completion of the cleaning operation. Upon issuance of the alert indicating completion of the cleaning operation, the electronic record associated with the lens 24 can be updated at step 155 to indicate that the lens 24 has been cleaned since its most-recent use with a patient, and is ready for use with a different patient.

Although the alerts described herein are all visual alerts displayed by the touch-sensitive display panel 14, alternate embodiments can include any type of alert including one or more of a visual and audible notification. For example, if the technician selects a checkbox 70 shown in FIG. 2 within the interface 40, the computer system 10 can play music while the time 56 is counted down. The music can optionally be terminated upon completion of the cleaning operation when the timer expires.

Further, embodiments of the system and method described herein can optionally include a sensor provided to each cleaning station 32 to sense when a lens 24 inserted therein is removed. Thus, if a lens 24 being subjected to a cleaning operation is removed before the time 56 of the cleaning operation expires, the computer system 10 can receive a signal indicating such a condition and update in the electronic record that cleaning of that lens 24 has not been completed since the lens 24 was last used.

In response to completion of the cleaning operation, the computer system 10 updates the status of the lens 24 to be ready for use at step 155. Should the cleaning operation be interrupted prior to completion, the computer system 10 can revert to the default status of not ready for use to minimize the likelihood of premature use of the lens 24.

In addition to completion of the cleaning operation, the lens 24 may be required to pass a pressure test to determine whether the sheath 26 is intact to minimize the entry of fluids into an interior of the lens 24. The technician an scan the barcode 34 provided to that lens 24 and conduct the pressure test by elevating a pressure within the sheath 26. If the lens 24 passes the pressure test, the technician can manually select the appropriate menu item displayed by the touch-sensitive display panel 14 to indicate successful completion of the pressure test. The computer system 10 can again update the electronic record associated with the lens 24 to indicate passage of this test.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used herein, such term is intended to be inclusive in a manner similar to the term "comprising" as "comprising" is interpreted when employed as a transitional word in a claim.

What is claimed is:

1. A method of monitoring a status of a medical instrument, the method comprising:
   receiving, using an input peripheral associated with a computer terminal, a code associated with the medical instrument to be subjected to a cleaning operation after a previous use of the medical instrument;
   receiving a predetermined length of time that the medical instrument is to be exposed to a cleaning agent before the cleaning operation can be considered complete;
   initiating a timer for monitoring a duration of the cleaning operation;
   receiving an indication that the medical instrument has been removed from the cleaning agent before the predetermined length of time expires based on the timer;
   in response to said receiving the indication, causing an electronic record that is associated with the medical instrument and is linked to the code to reflect that the medical instrument has not completed the cleaning operation;
   in response to completion of the cleaning operation determined based on the timer, updating a status of the medical instrument in the electronic record associated with the medial instrument stored in a non-transitory computer-readable medium to indicate that the medical instrument has been cleaned; and
   issuing an indication that the cleaning operation being performed on the medical instrument is complete.

2. The method according to claim 1 further comprising, in response to receiving the code, initiating a query of the electronic record to determine the status of the medical instrument.

3. The method according to claim 2, wherein said query retrieves a cleaning status from the electronic record associated with the medial instrument to determine whether the medical instrument has already been subjected to the cleaning operation after a most-recent previous use of the medical instrument.

4. The method according to claim 3 further comprising issuing an alert to warn that the medical instrument has not been subjected to the cleaning operation in response to retrieval of the cleaning status from the electronic record.

5. The method according to claim 4 further comprising issuing an alert that the medical instrument has successfully completed the cleaning operation in response to retrieval of the cleaning status from the electronic record.

6. The method according to claim 1, wherein the input peripheral comprises a computer-readable code reader and the code comprises a computer-readable code.

7. The method according to claim 6, wherein the computer-readable code reader is a barcode scanner and the computer-readable code is a barcode.

8. The method according to claim 1 further comprising, in response to receiving said code, initiating a query of the electronic record to retrieve a lockout status of the medical instrument indicating whether it has been determined that the medical instrument includes a condition that is to be addressed prior to subsequent use of the medical instrument with a patient.

9. The method according to claim 8, wherein the condition includes a breach of a housing provided to the medical instrument through which a contaminant can enter an interior of the medical instrument when the medical instrument is used with the patient.

10. The method according to claim 9 further comprising, in response to retrieving the lockout status indicating that the medical instrument includes the breach of the housing, issuing an alert for warning against use of the medical instrument before the breach of the housing has been resolved.

11. The method according to claim 1 further comprising:
monitoring a status of a cleaning solution to be used during the cleaning operation; and
in response to determining that the cleaning solution has exceeded its useful life, issuing an alert indicative of expiration of the cleaning solution.

12. The method according to claim 11 further comprising:
receiving a signal indicative of replacement of the cleaning solution that has exceeded its useful life with fresh cleaning solution;
in response to receiving said signal, determining an expiration date of the fresh cleaning solution;
monitoring a status of the fresh cleaning solution; and
issuing an alert that the fresh cleaning solution has exceeded its useful life on the expiration date.

13. The method according to claim 1 further comprising:
receiving a selection of a first cleaning station, from among a plurality of available cleaning stations, to be used for performing the cleaning operation of the medical instrument; and
updating the electronic record associated with the medical instrument to reflect the selection of the first cleaning station as being selected for the cleaning operation.

14. The method according to claim 13, wherein said receiving the selection of the first cleaning station comprises receiving a manual selection of the first cleaning station displayed by a display panel from among the plurality of available cleaning stations displayed by the display panel.

15. The method according to claim 1, wherein the timer establishes a predetermined minimum length of time for which the medical instrument is required to be exposed to a cleaning fluid at a cleaning station identified by a cleaning station code received using the input peripheral before the cleaning operation is considered complete.

16. A method of monitoring a status of an endoscopic medical instrument comprising a housing that is to be at least partially inserted into a patient, the method comprising:
receiving, using a barcode scanner, a code associated with the endoscopic medical instrument to be subjected to a cleaning operation after a previous use of the endoscopic medical instrument with another patient;
initiating a query of an electronic record associated with the endoscopic medical instrument and stored in a non-transitory computer-readable medium to determine whether the endoscopic medical instrument was cleaned after a most-recent use of the endoscopic medical instrument with the another patient;
receiving a selection of a first cleaning station, from among a plurality of available cleaning stations, to be used for performing the cleaning operation of the endoscopic medical instrument;
in response to said receiving the selection of the first cleaning station, initiating a timer for timing a duration of the cleaning operation;
receiving an indication that the endoscopic medical instrument has been removed from a cleaning agent utilized for the cleaning operation before the duration of the cleaning operation has expired as determined by the timer;
in response to said receiving the indication, causing the electronic record linked to the barcode to reflect that the endoscopic medical instrument was removed from the cleaning agent before the duration timed by the timer has expired;
in response to completion of the cleaning operation determined based on the timer, updating a status of the endoscopic medical instrument in the electronic record to indicate that the endoscopic medical instrument has been cleaned since the most-recent use with the another patient; and
issuing an indication that the cleaning operation being performed on the endoscopic medical instrument is complete.

17. The method according to claim 16 further comprising:
monitoring a status of cleaning solution provided to the first cleaning station to be used during the cleaning operation; and
in response to determining that the cleaning solution has exceeded its useful life, issuing an alert indicative of expiration of the cleaning solution.

18. The method according to claim 17 further comprising:
receiving input that the cleaning solution that has exceeded its useful life has been replaced with fresh cleaning solution;
in response to receiving said input, determining an expiration date of the fresh cleaning solution;
monitoring a status of the fresh cleaning solution; and
issuing an alert that the fresh cleaning solution has exceeded its useful life on the expiration date.

19. A system for cleaning a medical instrument between uses with different patients, the system comprising:
a cleaning station storing a cleaning solution in which a housing provided to the medical instrument is to be at least partially submerged during a cleaning operation; and
a computer system for monitoring a status of the cleaning operation, the computer system comprising:

a computer-readable-code reader that is operable to read a computer-readable code to distinguish the medical instrument from another medical instrument;

a display device for displaying an interface comprising a virtual cleaning station corresponding to the cleaning station;

a sensor that senses removal of the medical instrument from the cleaning station;

a non-transitory computer-readable medium for storing an electronic record associated with the medical instrument and linked to the computer-readable code; and a processor for executing computer-executable instructions to perform a method comprising:

receiving, using the computer-readable-code reader, the computer-readable code associated with the medical instrument to be subjected to the cleaning operation;

initiating a query of the electronic record to determine whether the endoscopic medical instrument was cleaned after a most-recent use of the endoscopic medical instrument;

initiating a timer for timing a duration of the cleaning operation;

receiving an indication transmitted by the sensor that the medical instrument has been removed from the cleaning station before the cleaning operation is complete based on the timer;

in response to said receiving the indication, causing the electronic record linked to the computer-readable code to reflect a premature termination of the cleaning operation;

in response to completion of the cleaning operation determined based on the timer, updating a status of the medical instrument in the electronic record to indicate that the medical instrument has been cleaned since the most-recent use; and issuing an indication that the cleaning operation being performed on the medical instrument is complete.

\* \* \* \* \*